United States Patent [19]

Miyata et al.

[11] 4,254,779

[45] Mar. 10, 1981

[54] BRAIN WAVE ANALYSIS APPARATUS FOR USE IN DIAGNOSING LIVING BODY CONDITIONS

[75] Inventors: Seiji Miyata, Ohi; Masatake Akagawa, Yachiyo; Masahiro Yamamoto; Noboru Inoue, both of Tokyo, all of Japan

[73] Assignee: Asahi Medical Co., Ltd., Tokyo, Japan

[21] Appl. No.: 915,048

[22] Filed: Jun. 9, 1978

[30] Foreign Application Priority Data

Mar. 15, 1978 [JP] Japan ................................. 53/30205

[51] Int. Cl.³ ............................................ A61B 5/00
[52] U.S. Cl. .................................... 128/731; 364/417
[58] Field of Search ........... 128/2.06 R, 2.1 B, 2.1 M, 128/2.1 R, 2.1 Z, 702–704, 731–733; 324/77 R, 77 A; 364/413–417, 487, 554–555, 734, 812; 235/92 MT

[56] References Cited

U.S. PATENT DOCUMENTS

| 3,087,487 | 4/1963 | Clynes | 128/2.1 B |
|---|---|---|---|
| 3,497,684 | 2/1970 | McKiernan | 364/554 |
| 3,623,477 | 4/1969 | Trent | 128/2.1 B |
| 3,626,168 | 7/1969 | Norsworthy | 364/554 |
| 3,725,690 | 4/1973 | Hjorth | 128/2.1 B |
| 3,880,147 | 4/1975 | Gruenke et al. | 128/2.06 A |
| 4,020,286 | 4/1977 | Ceci | 364/554 |
| 4,080,653 | 3/1978 | Bowes, Jr. et al. | 235/92 MT |

OTHER PUBLICATIONS

"Multi-Purpose Digital Computer for Research", Mnemotron Corporation, 45 S. Main St., Pearl River, N.Y.

Halliday, A. M., "Computing Techniques in Neurologic Diagnosis", British Medical Bulletin, vol. 24, No. 3, pp. 253–259.

Gevins, A. S. et al., "Automated Analysis of the Electrical Activity of the Human Brain (EEG)", Proc. of IEEE, vol. 63, No. 10, Oct., 1975, pp. 1382-1398.

Itil, T. M. et al., "Digital Comp. Classification of EEG Sleep Stages", EEG & Clin. Neurophys., 1969, 27:76-83.

Cox, Jerome R. et al., "Dig. Analysis of EEG, Blood Pressure Wave, and ECG", Proc. of IEEE, vol. 60, No. 10, Oct., 1972, pp. 1137-1164.

Hirose, K., "Quantitative Electromyography-A Method by Computer Analysis", Electromyogr. & Clinical Neurophys. 1972, No. 5, 12, pp. 421-429.

Kwatny, E. et al., "An Application of Signal Processing Techniques to the Study of Myselectric Signals", IEEE BME Trans., vol. 17, No. 4, Oct. 1970, pp. 303-313.

Dascalov, I. K., "EEG Pre-Processing by an On-Line Amplitude and Frequency Analyzer", Med. & Biol. Engr., May, 1974, vol. 12, No. 3

Primary Examiner—Robert W. Michell
Assistant Examiner—Francis J. Jaworski
Attorney, Agent, or Firm—Pollock, Vande Sande and Priddy

[57] ABSTRACT

In a brain-wave analysis apparatus, an electrical brain-wave signal is analyzed for purposes of diagnosis by detecting the time interval between adjacent ones of the intersections of the brain-wave signal with a predetermined level, and the peak value and the wave-form area of the brain-wave signal in the said time interval, or the amplitude value of the brain-wave signal every constant period of time. The said time intervals, peak values, wave form areas, and amplitude values are each classified according to their magnitude, accumulated and stored; and said information is used to prepare histograms. The histograms are analyzed by a processor to obtain their standard deviations, and variations in the standard deviations with time are displayed or recorded to provide a basis for diagnosing living body conditions.

10 Claims, 21 Drawing Figures

BRAIN WAVE ANALYSIS APPARATUS FOR USE IN DIAGNOSING LIVING BODY CONDITIONS

BACKGROUND OF THE INVENTION

This invention relates to apparatus in which the brain waves of a living body are detected and processed for the purpose of diagnosing living body information such as dysfunction of the brain itself, the kidney, the liver, etc.

There has been employed heretofore a method of diagnosing epilepsy, a brain injury resulting from a traffic accident, encephaloma, etc. on the basis of the waveforms of electrical brain-wave signals recorded on a recording paper. Further, an attempt has been made heretofore to find a correlation between the recorded waveforms of the brain waves and other living body informaton. Also an attempt has been made to diagnose a pathological condition by processing the electrical brain-wave signals. However, there has not yet been put to practical use, a satisfactory method of providing correct diagnostic information. Especially in the past, it has been contemplated to detect abnormalities separately appearing in the waveform of the brain-wave signal, or differences between brain waves detected from a plurality of points on the head. Accordingly, abnormalities in the brain waves cannot be detected when appearing steadily.

For detecting to what extent dialysis by an artificial kidney has proceeded, there has been proposed a method of measuring the weight of a patient subjected to the dialysis, based on the fact that his weight decreases as toxins are eliminated by the dialysis from his body. With this method, however, it is necessary to accurately check the weight of the patient in his normal conditions, but the detection of an absolute value of his weight is difficult because the weight in normal conditions differs before and after urination, for instance, and accordingly it is impossible to correctly detect completion of the dialysis. Further, if the dialysis is not carried out correctly, water in the blood is also eliminated from the body, also making it difficult to correctly detect completion of the dialysis.

Another method that has heretofore been employed is to measure the amounts of, for example, urea, creatinine, uric acid or the like in the blood of a patient before and after dialysis and to determine to what extent the patient should be subjected to dialysis on the basis of the data and the time for the previous dialysis. However, since preparation of such data is time-consuming, it is impossible to check the dialyzing condition during dialysis. Consequently, the time for dialysis is assumed from data obtained for each dialysis previously effected, so that completion of the dialysis cannot be detected in the case where the condition of the patient changes.

An object of this invention is to provide a living body information diagnosing apparatus which enables the detection of steady abnormalities appearing in the waveform of a brain-wave signal, thereby to ensure a correct diagnosis of living body information.

Another object of this invention is to provide a living body information diagnosing apparatus with which it is possible to detect not only unsteady but also steady abnormalities from variations in the waveform of a brain-wave signal, thereby to enable diagnosing the condition of a disease as well as identifying a disease.

Another object of this invention is to provide a living body information diagnosing apparatus with which it is possible to continuously detect the progress of dialysis by an artificial kidney and to check whether or not dialysis is required for the treatment of a patient.

Still another object of this invention is to provide a living body information diagnosing apparatus with which it is possible to diagnose encephalitis from hepatitis.

SUMMARY OF THE INVENTION

According to this invention, brain waves are detected in the form of an electrical signal, from which is derived at least one of the parameters relating to its waveform, that is, the value obtained by counting the number of intersections of the electrical brain-wave signal with a constant level (inclusive of the zero level) for a predetermined period of time, a standard deviation of the distribution of dispersion of the time intervals of the intersections of the brain-wave signal with the constant level, a standard deviation of the distribution of dispersion of the peak value of the brain-wave signal between adjacent ones of its intersections with the constant level, a standard deviation of the distribution of dispersion of the area of the brain-wave signal between adjacent ones of its intersections with the constant level, and a standard deviation of the distribution of the amplitude probability density of the brin-wave signal within a certain period of time. The parameter thus detected with the lapse of time is recorded on a recording paper for display, or displayed on a cathode ray tube display or a numeric display. In this manner, the initial value of the parameter is stored and compared with the values of the parameter being detected currently, providing a basis for diagnosing various living body conditions.

BRIEF DESCRIPTION OF THE DRAWINGS

FIGS. 11 A–D are exemplary histogram plots of brain wave signal amplitude, peak value, area and time interval between zero-crossing points, respectively;

DESCRIPTION OF THE PREFERRED EMBODIMENTS

Figure 1:
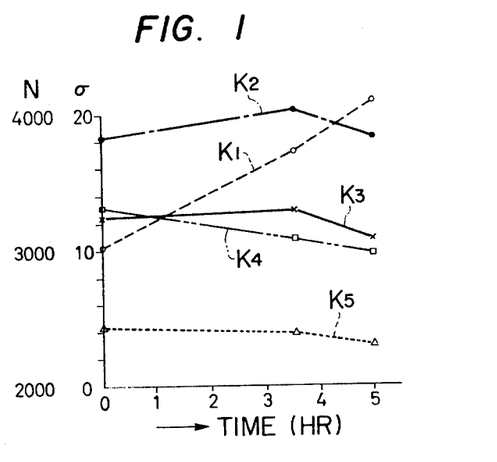
FIGS. 1 and 2 are graphs showing variations in various parameters of brain-wave signals during dialysis by an artificial kidney.
Figure 2:
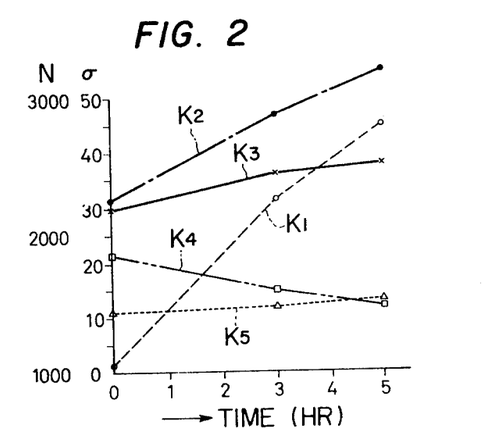

FIGS. 1 and 2 show experimental data of the above-said parameters measured in connection with different test subjects during dialysis by an artificial kidney. In FIGS. 1 and 2, the curve $K_1$ represents the number of intersections of an electrical brain-wave signal with a certain level within a certain period of time, the curve $K_2$ a standard deviation of a histogram of the entire emplitude of the brain-wave signal within a certain period of time, the curve $K_3$ a standard deviation of a histogram of the peak value of the brain-wave signal between adjacent ones of its intersections with the said certain level, the curve $K_4$ a standard deviation of a histogram of the time intervals between adjacent ones of the intersections of the brain-wave signal with the said certain level, and the curve $K_5$ a standard deviation of a histogram of the waveform area of the brain-wave signal between adjacent ones of its intersections with the predetermined level. In FIGS. 1 and 2, the abscissa represents time and the ordinate represents the sample number N and the standard deviation $\delta$. As dialysis proceeds, the curves $K_1$, $K_2$ and $K_3$ rise but the curve $K_4$ falls. From these curves, it is possible to check the progress and completion of the dialysis. That is, by storing an initial value of at least one of these parameters and comparing it with the corresponding data being detected currently, it can be determined to what extent the dialysis has proceeded. The reason for such relationships between the condition of dialysis and brain waves is considered to be due to the following fact:

Namely, before dialysis, relatively many toxins exist in the blood and enter into the brain to affect its function to cause dispersion in the brain-wave waveform, but as the dialysis proceeds, the brain action becomes active and brain waves frequently occur to decrease dispersion in the waveform.

Figure 3:
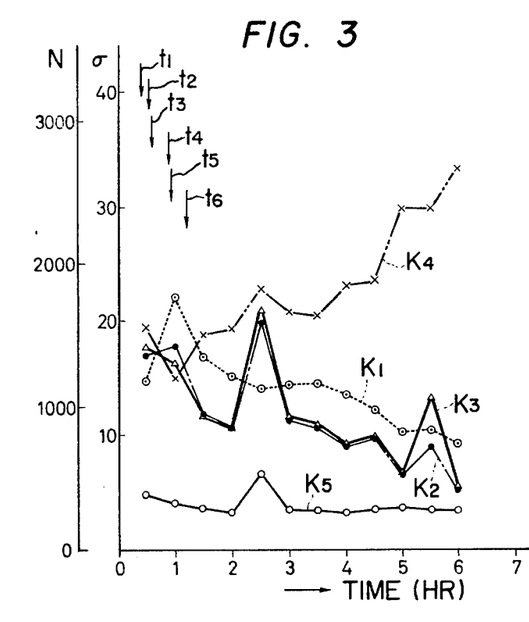
FIG. 3 is a graph showing variations in various parameters of brain-wave signals when the liver of a dog was extracted.

FIG. 3 shows variations in brain-wave parameters of a dog after his liver was removed. The curves $K_1$ to $K_5$ represent the same parameters as those in FIGS. 1 and 2. The portal vein was partly closed at a moment $t_1$ and opened at a moment $t_2$; the inferior venacava was closed at a moment $t_3$; the portal vein was entirely closed at a moment $t_4$; the liver was extracted at a moment $t_5$; and the portal vein and the inferior venacava were respectively opened at a moment $t_6$. With the lapse of time, the curves $K_1$, $K_2$, $K_3$ and $K_5$ fall and the curve $K_4$ rises. From these curves, it is possible to diagnose hepatitis, hepatocirrhosis, hepatic tumor and encephalitis from such liver trouble and to check the condition of the disease.

Figure 4:
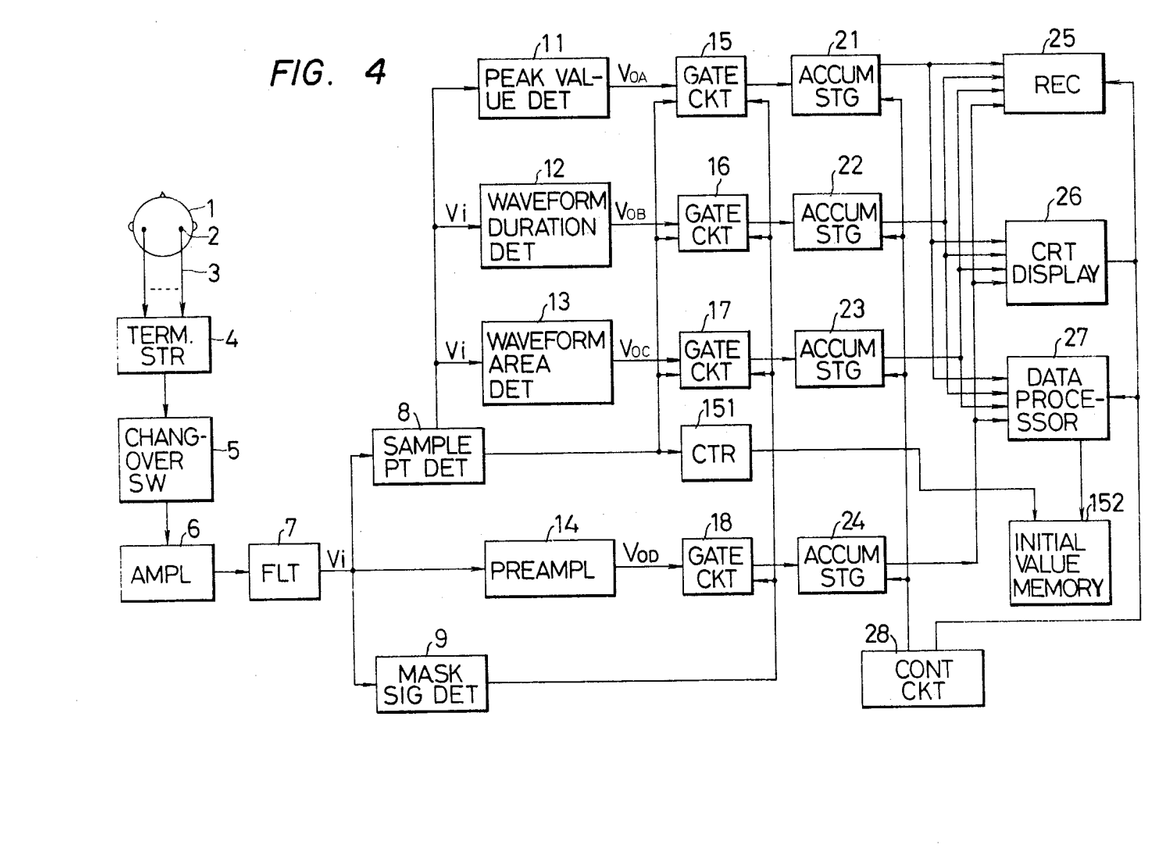
FIG. 4 is a block diagram illustrating an embodiment of the living body diagnosing apparatus of this invention.

Referring now to FIG. 4, a description will be given with regard to an embodiment of the living body information diagnosing apparatus of this invention.

Electrodes 2 are respectively attached to a plurality of induction points on the head 1 of a test subject and connected to an induction point changeover switch 5 via leads 3 and an electrode terminal strip 4. Electrical signals of brain waves (hereinafter referred to as the brain-wave signal) from one of the induction points selected by the switch 5 are amplified by an amplifier 6. The above construction is identical with those of conventional electroencephalographs. The electroencephalograms heretofore employed usually have eight to twelve induction points. In the case of simultaneously observing brain waves from a plurality of points of the brain, a plurality of systems are provided following the amplifier 6 and the brain-wave signals from different induction points are respectively applied to the several systems.

The output from the amplifier 6 is provided to a filter 7 to eliminate unnecessary components. A low-pass filter or high-pass filter, or a combination of them is used as the filter 7 depending upon the measuring conditions used. The output signal Vi from the filter 7 is applied to a sample point detector 8 and a mask signal detector 9 for eliminating an unnecessary signal to provide a sampling command signal and a masking command signal, respectively.

The brain-wave signal Vi is applied to signal processing units such as a peak value detector 11, a waveform duration detector 12, a waveform area detector 13 and and a preamplifier 14 for detecting the density of the amplitude probability, by which signal processing is achieved according to the respective circuits. At the same time, sampling commands are applied to gate circuits 15 through 17 respectively provided at the next stages of the signal processing circuits 11 through 13, and to accumulating storage units 21 through 23 respectively cascade-connected to the gate circuits. Sampling commands to a gate circuit 18 provided at the next stage of the preamplifier 14 and a data accumulating storage unit 24 cascade-connected to the gate circuit 18 are sampling commands of a constant period provided from a pulse generator, by which is measured the distribution of the density of the amplitude probability. The data accumulating storage units 21 through 24 have the function of adding and accumulating, upon each occurrence of the sampling command, analog input voltages in memories, each provided for the magnitude of each input voltage.

The data stored in the data accumulating storage units 21 though 24 are each converted to an analog value and recorded by a recorder 25 as a hard copy, or displayed on the screen of a CRT display 26 for monitoring the data contents. Further, the data from the accumulating storage units 21 through 24 are applied in digital form to a data processor 27 for data computation processing described later, providing a certain evaluation. The data accumulating storage units 21 through 24, the recorder 25, the display 26 and the data processor 27 are controlled by a control circuit 28. The number of intersections of the brain-wave signal with the zero level within a predetermined period of time is counted by an intersection number counter 151. Initial values of standard deviations of the distributions of dispersion of the various data obtained with the data processor 27 and the initial count value of the intersection number counter 151 are respectively stored in an initial value memory circuit 152.

Figure 5:
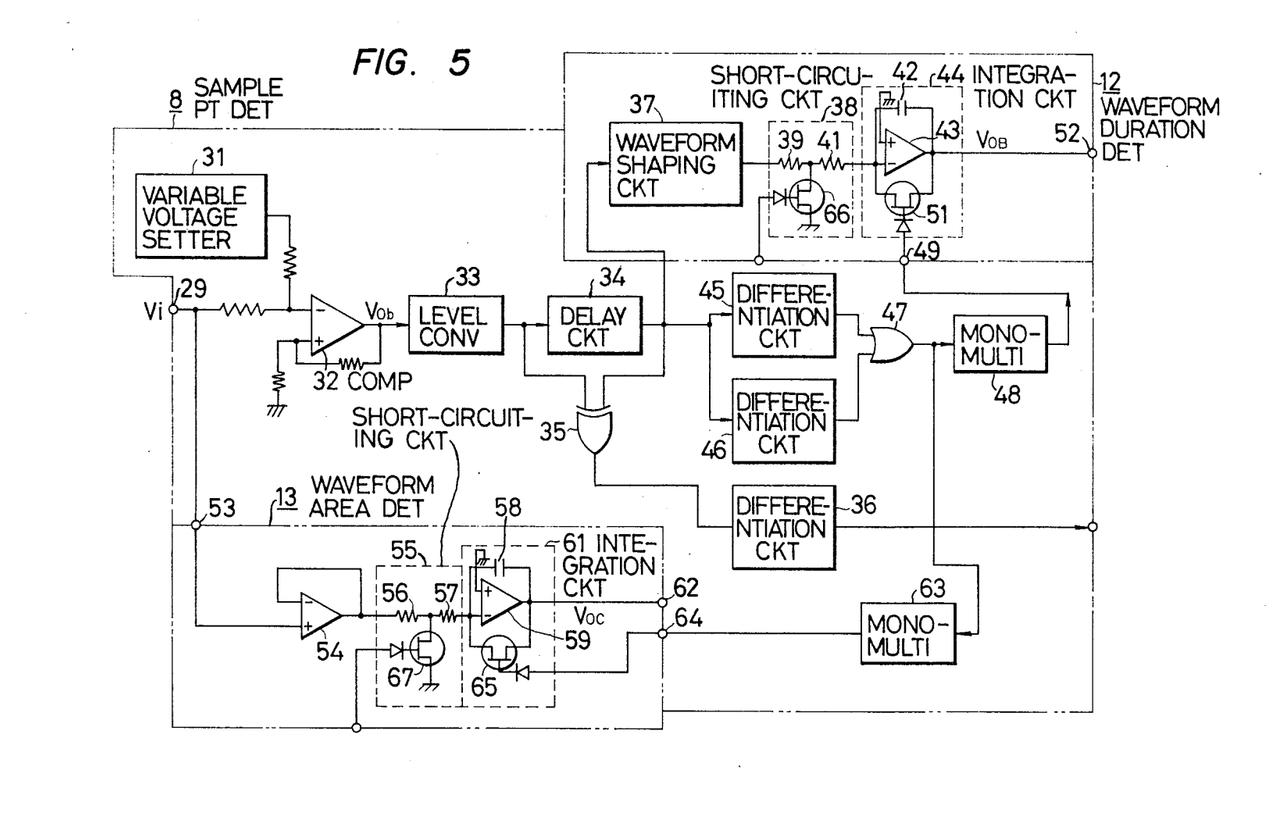
FIG. 5 is a block diagram showing an example of a sample point detector, a time interval detector, and an area detector utilized in this invention.

The respective parts of the apparatus shown in FIG. 4 will now be described in detail. Since the apparatus can be made up with linear ICs and digital ICs which are semiconductor ICs now on the market, the following will describe the respective parts using logic terms. FIG. 5 shows the sample point detector 8, the waveform duration detector 12 and the waveform area detector 13. The brain-wave signal Vi applied to an input terminal 29 is compared by a comparator 32 with a reference voltage from a variable voltage setter 31. The level of the variable voltage setter 31 is set so that the comparator 32 may achieve the abovesaid comparison at a level near the zero crossing point of the input brain-wave signal Vi. This level is changed with that of the brain-wave signal and may preferably be the zero crossing point of the signal Vi but is determined according to circumstances.

Figure 10:
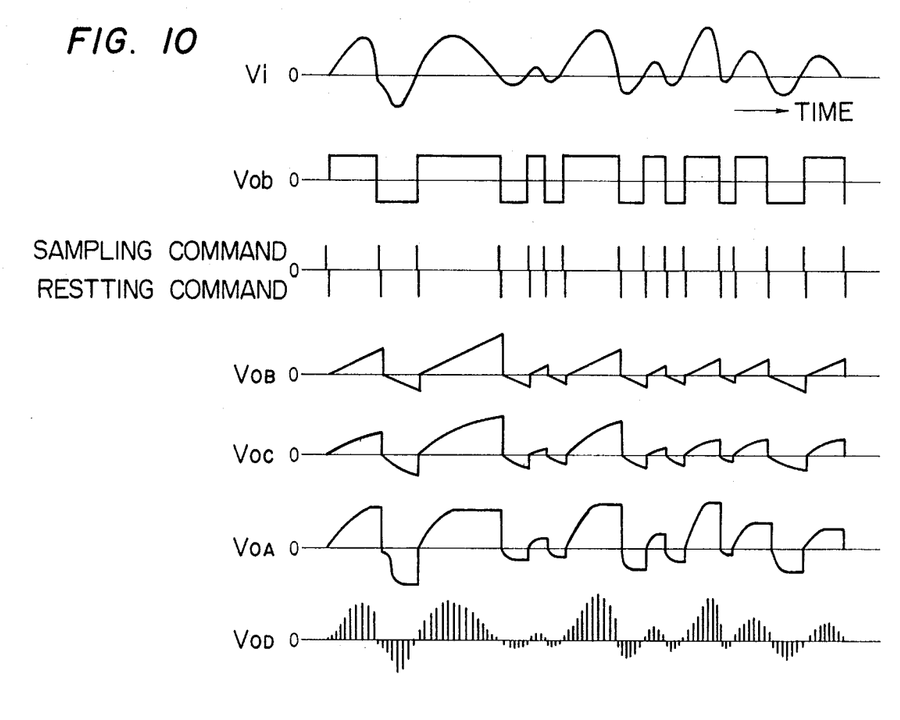
FIG. 10 is a waveform diagram showing an example of signal processing in this invention.

Accordingly, the output from the comparator 32 is applied to a level converter 33 in the form of a rectangular wave output Vob such as shown in FIG. 10 which changes from positive to negative or from negative to positive substantially at each zero crossing point of the input brain-wave signal Vi. In this case, if DC components are added to the rectangular wave signal, the DC components must naturally be cut off. The rectangular wave signal Vob is subjected by the level converter 33 to level conversion to the TTL level, thereafter being supplied to a waveform delay circuit 34 and an exclusive OR circuit 35. The rectangular wave of the TTL level corresponding to the input brain-wave signal Vi is delayed by the waveform delay circuit 34 for 1 to 2 $\mu$sec, and an exclusive OR operation of the delayed waveform and the undelayed one is performed by the exclusive OR circuit 35. A first falling point of the output signal from the exclusive OR circuit 35 is picked up by a waveform differentiation circuit 36 and used as a sampling command signal. The sampling command signal is also applied to the intersection number counter 151 to cause it to repeat counting for a predetermined period of time.

The output from the waveform delay circuit 34 is converted by a waveform shaping circuit 37 of the waveform duration detector 12 from the TTL level to a rectangular wave signal Vob having both positive and negative polarities. The rectangular wave signal Vob is provided via resistors 39 and 41 of a short-circuiting circuit 38 to an integration circuit 44 which is composed of an integrating capacitor 42 and an operational amplifier 43. The circuit 38 is a short-circuiting one which is cut off when the input brain-wave signal Vi is zero. On the other hand, the rising and falling points of the rectangular wave from the waveform delay circuit 34 are detected by waveform differentiation circuits 45 and 46, respectively, and the detected outputs are applied via an OR circuit 47 to a monostable multivibrator 48 to drive it. Only during the operating period of the monostable multivibrator 48, a reset signal is supplied via an input terminal 49 to a FET switch 51 to turn it ON, through which the charge stored in the integrating capacitor 42 is discharged to reset the integration circuit 44. With such an arrangement, the time between adjacent ones of the zero crossing points of the input brain-wave signal Vi is converted to a voltage $V_{OB}$ and provided at an output terminal 52 of the integration circuit 44.

The input brain-wave signal Vi from the input terminal 29 is applied to an amplifier 54 via an input terminal 53 of the waveform area detector 13. The output from the amplifier 54 is provided via resistors 56 and 57 of short-circuiting circuit 55 to an integration circuit 61 which is composed of an integrating capacitor 58 and an operational amplifier 59. The circuit 55 is cut off when the input brain-wave signal Vi is zero, as is the case with the aforesaid circuit 38. The integrated output $V_{OC}$ from the integration circuit 61 is derived at its output terminal 62 (see FIG. 10). Only during the operating period of a monostable multivibrator 63 which is triggered by the output from the aforesaid OR circuit 47, a reset signal is applied via a reset signal input terminal 64 to a FET switch 65 to turn it ON, resetting the integration circuit 61. With the above arrangement, the signal $V_{OC}$ indicative of the area of the waveform between adjacent zero crossing points of the brain-wave signal is provided at the terminal 62. In FIG. 5, commands to the short-circuiting circuits 38 and 55 are provided from the mask signal detector 9 described later on and, in such a case, FET switches 66 and 67 are turned ON, through which the potentials at the connection points of the resistors 39 and 41 and the resistors 56 and 57 are respectively reduced to substantially zero.

Figure 6:
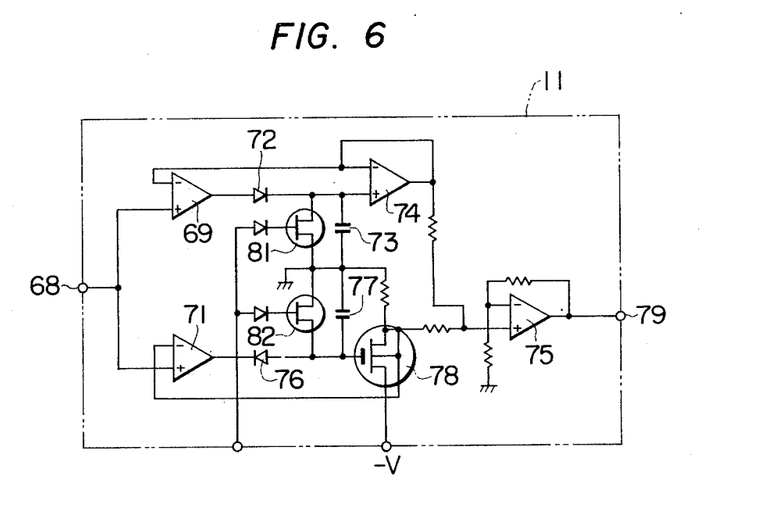
FIG. 6 is a block diagram showing an example of a peak value detector used in this invention.

Turning now to FIG. 6, the peak point detector 11 will be described. The input brain-wave signal Vi is supplied via an input terminal 68 to non-inverting input ends of buffer operational amplifiers 69 and 71, and the positive side of the input brain-wave signal Vi is charged in a capacitor 73 via a diode 72. The voltage of the capacitor 73 is supplied via a buffer operational amplifier 74 to a non-inverting input end of an adding operational amplifier 75. On the other hand, the negative side of the input brain-wave signal Vi from the terminal 68 is applied from the buffer operational amplifier 71 to a capacitor 77 via a diode 76. The voltage charged in the capacitor 77 is provided via a buffer FET 78 to a non-inverting input end of an adding operational amplifier 75 of the next stage. In this manner, the peaks of the positive and negative sides of the input brain-wave signal Vi at the respective polarity inversion points, i.e. zero crossing points of the signal Vi, are charged and held in the capacitors 73 and 77 and alternately appear as the output $V_{OA}$ (see FIG. 10) at an output terminal 79 of the adding operational amplifier 75. The resetting of this operation is effected as follows:

The output from a monostable multivibrator (not shown) which is triggered by the output from the OR circuit 47 mentioned above with respect to FIG. 5, is applied to FET switches 81 and 82 to turn them ON during the operation of the monostable multivibrator, thereby discharging the charges of the capacitors 73 and 77. With the above arrangement, the peak value $V_{OA}$ of the voltage of the input brain-wave signal Vi between adjacent ones of its zero crossing points, is derived at the output terminal 79.

Figure 7:
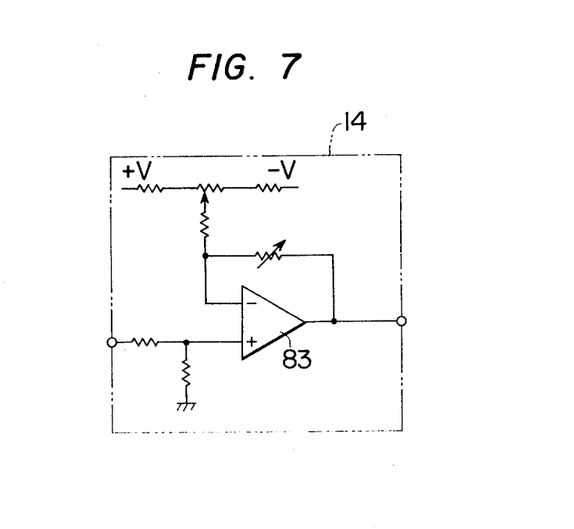
FIG. 7 is a connection diagram illustrating an example of a preamplifier employed in this invention.
Figure 8:
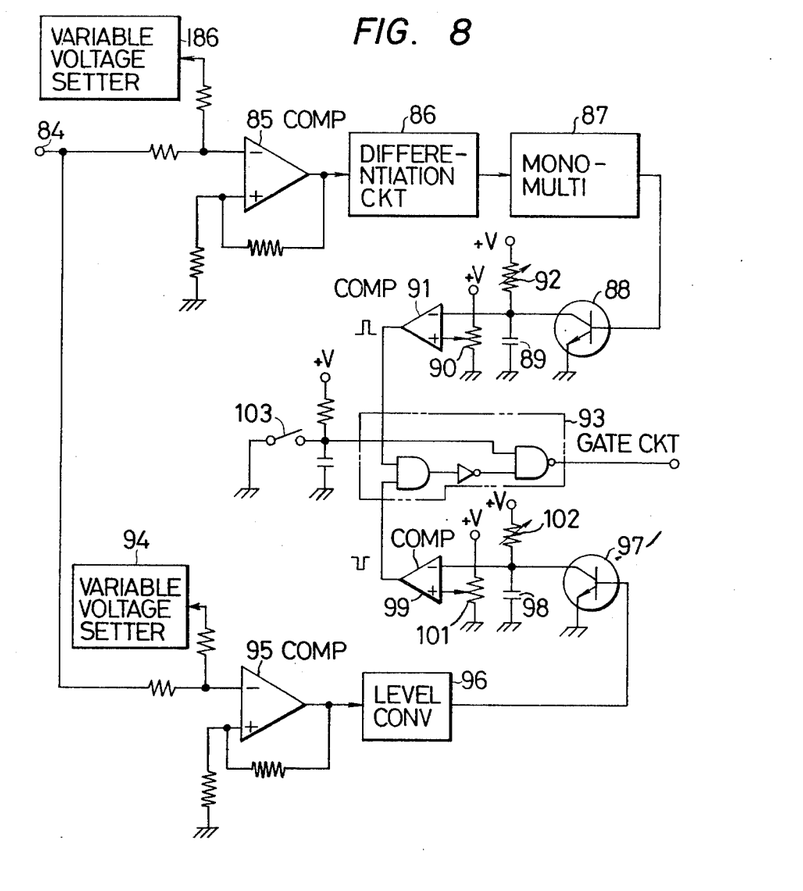
FIG. 8 is a circuit diagram showing an example of a mask signal detector.

The preamplifier 14 for obraining a histogram of the entire amplitude of the brain-wave signal comprises an operational amplifier 83, for instance, as shown in FIG. 7. The mask signal detector 9 produces a signal for inhibiting signal processing when the input brain-wave signal Vi is too small or too large, and has a construction such, for example, as shown in FIG. 8. The input brain-wave signal Vi from an input terminal 84 is applied first to a comparator 85 for comparison with a reference voltage from a variable voltage setter 186, and when the input brain-wave signal is larger than the reference voltage, the comparator 85 provides a constant positive voltage. The comparator output is subjected to level conversion by a level converter (not shown), after which its rise is extracted by a differentiation circuit 86 and, by the output therefrom, a monostable multivibrator 87 is triggered. The monostable multivibrator 87 is the retrigger type; namely when the time between adjacent positive sides of the waveform of the input brain-wave signal Vi is shorter than a preset operating time of the monostable multivibrator 87, the multivibrator output is further retained at a high level by the subsequent rising pulse. This high-level output turns ON a transistor switch 88 to short-circuit a capacitor 89. A comparator 91 compares the voltage of the capacitor 89 with a voltage resulting from the division of a power source voltage V+ with a variable resistor 90. When the voltage of the capacitor 89 has exceeded the divided output voltage provided by variable resistor 90, the output from the comparator 91 becomes zero-level. The connection point of the collector of the transistor switch 88 and the capacitor 89 is connected via a variable resistor 92 to the power source. If the input brain-wave signal Vi remains zero for longer than the time which is dependent upon the divided output voltage of the variable resistor 90 and the charging time constant determind by the variable resistor 92 and the capacitor 89, and if no trigger is supplied to the monostable multi-vibrator 87, the output from the comparator 91 becomes zero-level. As a result of this, the output from a gate circuit 93 which is supplied with the comparator output becomes low in level, thereby to inhibit the application of the sampling command signal to the next stage.

The input brain-wave signal Vi from the terminal 84 is also applied to a comparator 95, in which it is compared with a reference voltage from a variable voltage setter 94. When the input brain-wave signal Vi is larger than the reference voltage from the variable voltage setter 94, the output from the comparator 95 becomes a constant positive potential. The voltage level of the output from the comparator 95 is lowered by a level converter 96, and the output therefrom is provided to a transistor switch 97 to turn it ON, by which a capacitor 98 is short-circuited. A divided voltage of a variable resistor 101, which is supplied with a constant voltage, is provided to a comparator 99 where it is compared with the voltage of the capacitor 98. The comparator 99 produces a high-level or low-level output depending upon whether the voltage of the capacitor 98 is higher or lower than the divided voltage of the variable resistor 101. The capacitor 98 is connected via a variable resistor 102 to the power source. In the case where the input brain-wave signal Vi remains extremely large for a period of time which is determined by the divided output voltage of the variable resistor 101 and a charging time constant dependent upon the variable resistor 102 and the capacitor 98, the transistor switch 97 is turned ON to reduce the voltage of the capacitor 98 to the zero level, so that the output from the comparator 99 is also reduced to zero and the output from the gate circuit 93, which is supplied with the output from the comparator 99, becomes low-level, thus preventing the application of the sampling command signal to the next stage. By turning ON a switch 103, a low-level input is applied to the gate circuit 93 to compulsorily raise its output to a high level, by which it is also possible to inhibit such signal masking operations as described above.

Figure 9:
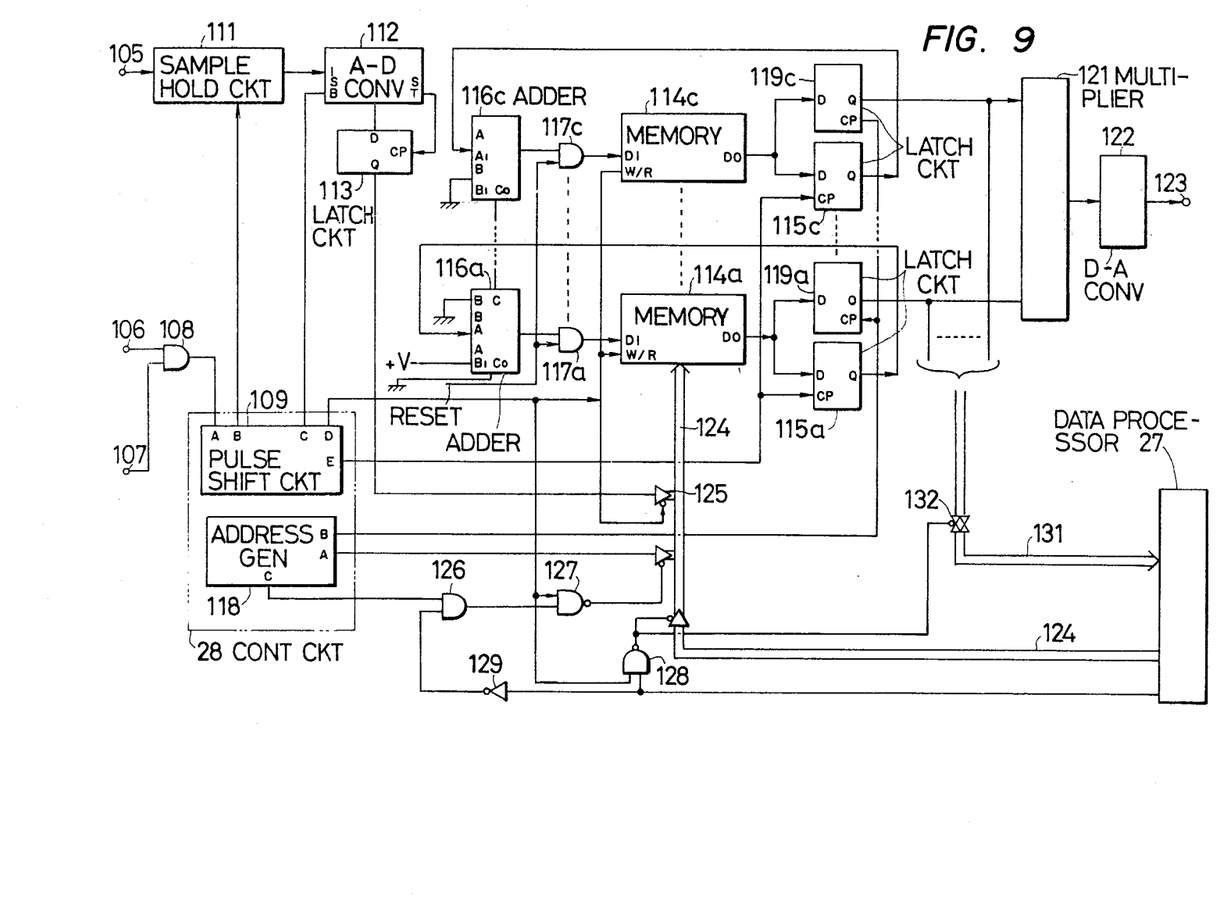
FIG. 9 is a block diagram illustrating an example of a data accumulating storage device utilized in this invention.

The outputs $V_{OA}$ to $V_{OD}$, respectively processed by the peak value detector 11, the waveform duration detector 12, the waveform area detector 13 and the preamplifier 14, are accumulated and respectively stored in the data accumulating storage units 21 through 24 in FIG. 4 under sampling commands. The accumulating storage units 21 through 24 can be formed identical in construction. For instance, as depicted in FIG. 9, the processed voltage, for example, $V_{OA}$ is provided to an analog input terminal 105. Upon application of a sampling command input to a sampling command terminal 106, a pulse shift circuit 109 is driven through a gate 108 supplied with the output from the gate circuit 93 in FIG. 8 through a terminal 107. A signal is provided from a terminal B of the pulse shift circuit 109 to a sample hold circuit 111 to sample and hold therein the analog input $V_{OA}$ applied to the analog input terminal 105. At this time, the pulse shift circuit 109 applies a signal from its terminal C to an A-D converter 112, in which the analog output voltage from the sample and hold circuit 111 is converted into a digital voltage. In this case, an A-D converter having 7 to 12 bits is used also from the economical point of view and in this embodiment an 8-bit A-D converter is employed.

Upon completion of the analog to digital conversion by the A-D converter 112, a signal is derived at its terminal ST and the converted digital value is latched in a latch circuit 113. This digital value is applied as an address via an address bus 124 to memories 114a to 114c to select one of them. The stored content of the selected memory is latched in a corresponding one of latch circuits 115a through 115c under a command from a terminal E of the pulse shift circuit 109, and the output from the latch circuit is provided to a corresponding one of adders 116a through 116c. The adders 116a through 116c are full adders such as Model 7483 sold by Texas Instrument, for example. Input terminals $B_2$, $B_3$ and $B_4$ of the adder 116a and input terminals $B_1$ through $B_4$ of the adders 116b and 116c are respectively grounded and only an input $B_1$ of the adder 116a is made high in level, by which only one bit is added to each of add input terminals $A_1$ through $A_4$.

The added outputs of parallel four bits from the adders 116a through 116c are provided via reset gates 117a to 117c to the memories 114a through 114c, respectively. In this embodiment, three memories with a capacity of 4 bits × 256 which are Model 2101 by Intel, for instance, are employed as the memories 114a through 114c, so that a 12-bit structure is shown. Write commands for the memories 114a through 114c are derived from a terminal D of the pulse shift circuit 109.

With the above arrangement, upon each occurrence of the sampling command, the analog value is converted to a digital value, and the digital value is applied to the memories 114a through 114c to read out them, and then 1 is added to the read out contents, and written again in the memories 114a through 114c. Next, except at the timing of the aforesaid addition and the memory read out of the data processor 27 (FIG. 4), addresses are sequentially applied by an address generator 118 to the memories 114a through 114c to read out their contents, which are latched in latch circuits 119a through 119c, and their outputs are supplied to a multiplier 121. The output from the multiplier 121 is provided to a D-A converter 122 to derive an analog output at a terminal 123 for input to the recorder 25 and the display 26 for monitoring. For the multiplier 121, it is possible to employ a bit slice method by the combined use of channel selector ICs. If the address of the address generator 118 is switched, for instance, at intervals of 0.5 or 1.0 sec., the analog output at the terminal 123 is used for the recorder 25, and if the address switching is achieved, for example, every 1 to 100 μsec, the analog output at the terminal 123 is used for the display 26.

When the addresses are applied from the latch circuit 113 through a gate 125 formed with a tri-state IC during addition, the buses 124 for the memories 114a through 114c are switched in the order of priority determined by the combination of an AND circuit 126, NAND circuits 127 and 128 and an inverter 129 so that the memories 114a through 114c may be switched in the order that their contents are displayed on the display 26 when read out of the data processor 27.

The outputs from the latch circuits 119a through 119c are provided via a tri-state buffer circuit 132 to a data bus 132 for reading out of the data processor 27. It is also possible to connect the memories 114a through 114c directly to the data bus 131 via the tri-state buffer circuit 132.

In FIG. 9, upon application of a low level output to the mask signal input terminal 107 from the gate circuit 93 in FIG. 8, the sampling command signal is inhibited from input to this data accumulating storage unit.

Next, for obtaining the amplitude histogram of the entire signal, the input brain-wave signal is applied to the analog input terminal 105 in FIG. 9 via the preamplifier 14 in FIG. 7. From a pulse generator (not shown) a pulse of a constant period is provided to the sampling command input terminal 106 in FIG. 9 at intervals of 100 μsec or 1 msec, for example, Upon each occurrence of the sampling command pulse, the operations described above are achieved to provide the amplitude histogram in the memories 114a through 114c.

Figure 11:
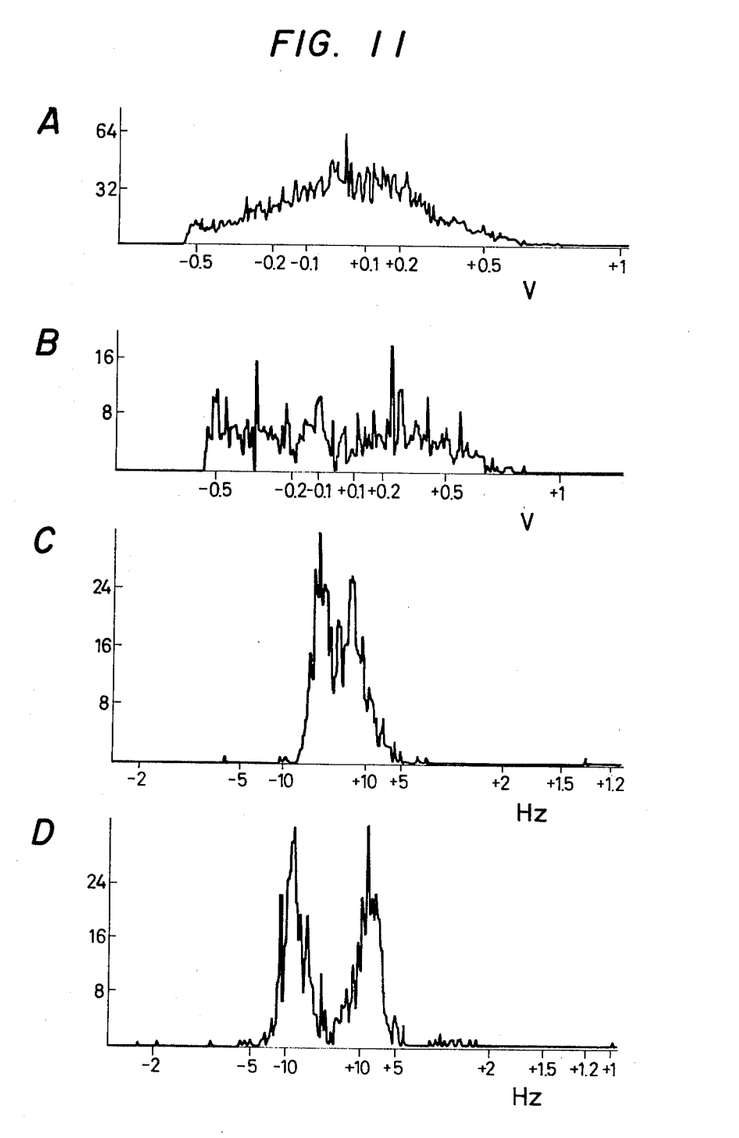

The results of the above processing operations are exemplified in FIG. 11. FIG. 11A is a histogram of the signal amplitude values obtained in the data accumulating storage unit 24, and the sample number N was 3000, the mean value $\bar{x}$ 135.8 and the standard deviation $\delta$ 31.32. FIG. 11B is a histogram of the peak values between the zero crossing points obtained in the accumulating storage unit 21, the sample number N being 595, the means value $\bar{x}$ 131.6 V and the standard deviation $\delta$ 35.1. FIG. 11C is a histogram of the area values between the zero crossing points obtained in the accumulating storage unit 22, the sample number N being 595, the mean value $\bar{x}$ 131.6 Hz and the standard deviation $\delta$ 10.3. FiG. 11D shows a histogram of the time intervals between adjacent zero crossing points obtained in the accumulating storage unit 23, the sample number N being 595, the mean value $\bar{x}$ 132.4 and the standard deviation $\delta$ 10.3.

From such histograms obtained in a relatively short time and in a relatively long time such as several hours, a histogram obtained in connection with each of a plurality of induction points, that is, measuring points, and a histogram obtained in connection with brain waves when a stimulus was given to a test subject, a diagnosis is made based on the pattern of the distribution curve of each histogram, that is, its shape or the pattern and frequency of a certain abnormality.

Figure 12:
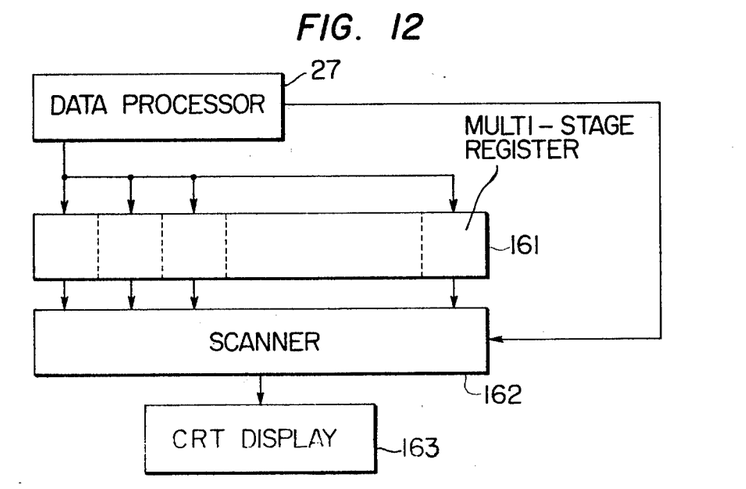
FIG. 12 is a block diagram illustrating an example of storing and display means employed in this invention.

Further, a diagnosis is made based on the mean value $\bar{x}$ and the standard deviation $\delta$ of each histogram and those $\bar{x}$ and $\delta$ of each abnormality group, that is, each population in each distribution curve. Namely, abnormalities are sampled and each compared with an initial value stored in the memory 152; in other words, variations in the sampled parameters with the lapse of time are detected, by which the condition of dialysis by an artificial kidney can be checked or the condition of nephritis or hepatitis, for instance, can be diagnosed, as described previously. From each histogram shown in FIG. 11, the deviation $\delta$ can easily be derived by the employment of an electronic computer in a short time. For example, as shown in FIG. 12, the standard deviation $\delta$, the number of level intersections of the brainwave signal or the like is stored in a multi-stage register 161 in a predetermined order every certain period of time. A scanner 162 is controlled by the data processor 27 so that the stored values of the register 161 are read out into a cathode ray tube display 163 in the order they were stored in the register 161. As a result, the curves shown in FIGS. 1 to 3 are displayed on the display 163. Also, it is possible to display a difference between the initial value and the currently detected value or the ratio of the latter value to the former in terms of percentage. By comparing the thus obtained results with similar patterns or data previously obtained in connection with the conditions of various diseases, it is possible to distinguish normality and abnormality of a test subject from each other, to identify a disease in the case of abnormality and to check the condition of the disease. These operations can also be achieved by the data processor 27 in a on-line manner.

Thus, the symmetry of the current brain-wave information with respect to the center of the head, a hypnotic wave, brain waves responsive to sound and light stimuli, an epiletic wave, brain waves in the cases of various diseases or in the case of unconsciousness, etc. can be faithfully compared with the brain waves of a healthy person in terms of statistics, so that the apparatus of this invention is of great utility in making a diagnosis, including the detection of the condition of a disease. Further, not only a trouble of the brain itself but also diseases such as nephritis, hepatitis and so on and their conditions can be identified. On top of that, it is also possible to correctly detect the moment of completion of dialysis using an artificial kidney and to check whether the dialysis is required or not.

Figure 13:
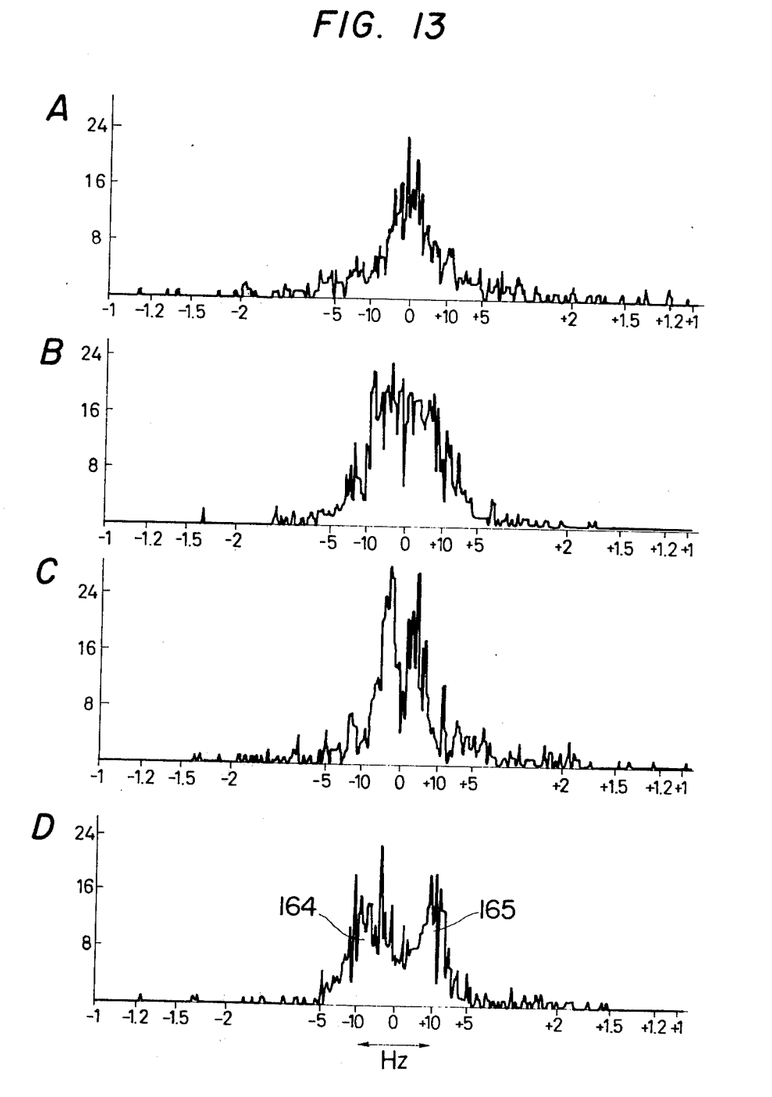
FIGS. 13A to 13D are graphs showing various examples of histograms of the time interval distribution.

FIGS. 13A to 13D show various patterns of the histogram of the distribution of the time intervals between adjacent intersections of the brain-wave signal with the zero level. In FIG. 13A, N=498, $\bar{x}$=129.9 and $\delta$=29.4; in FIG. 13B, N=799, $\bar{x}$=129.8 and $\delta$=17.8; in FIG. 13C, N=593, $\bar{x}$=132.2 and $\delta$=24.8; and in FIG. 13D, N=647, $\bar{x}$=131.4 and =21.6. FIG. 13D indicates the case of the test subject being awake at rest, with his eyes shut, and two humps 164 and 165 distinctly appear. Conversely, it is seen from the pattern of FIG. 13D that the test subject is in the abovesaid state. In this manner, a diagnosis can be made on the basis of the histogram pattern of the parameter of the brain-wave signal waveform. Therefore, this invention is very useful for diagnosing various living body information.

It will be apparent that many modifications and variations may be effected without departing from the scope of the novel concepts of this invention.

What is claimed is:

1. A brain wave analysis apparatus for use in diagnosing living body conditions, comprising:
    means for detecting brain waves from a living subject as an electrical brain-wave signal;
    means for detecting the intervals between adjacent ones of the intersections of the brain wave signal with a predetermined level;
    an accumulating storage unit for classifying the detected intervals according to magnitude and for accumulating and storing them to prepare a histogram;
    a data processor for analyzing the histogram and calculating a standard deviation; and
    display means for displaying variations in the standard deviation over a time period substantially longer than the time required to obtain one value of the standard deviation, thereby to obtain a display of the trend of said variations.

2. A brain wave analysis apparatus for use in diagnosing living body conditions, comprising
    means for detecting brain waves from a living subject as an electrical brain-wave signal;
    means for detecting the peak value of the brain-wave signal in the time interval between adjacent ones of the intersections of the brain-wave signal with a predetermined level;

an accumulating storage unit for classifying the detected peak values according to magnitude and for accumulating and storing them to prepare a histogram;

a data processor for analyzing the histogram and calculating a standard deviation; and display means for displaying variations in the standard deviation over a time period substantially longer than the time required to obtain one value of the standard deviation, thereby to obtain a display of the trend of said variations.

3. A brain wave analysis apparatus for use in diagnosing living body conditions, comprising means for detecting brain waves from a living subject as an electrical brain-wave signal;

means for detecting the waveform area value of the brain-wave signal in the time interval between adjacent ones of the intersections of the brain-wave signal with a predetermined level;

an accumulating storage unit for classifying the detected waveform area values according to magnitude and for accumulating and storing them to prepare a histogram;

a data processor for analyzing the histogram and calculating a standard deviation; and display means for displaying variations in the standard deviation over a time period substantially longer than the time required to obtain one value of the standard deviation, thereby to obtain a display of the trend of said variations.

4. A brain wave analysis apparatus for use in diagnosing living body conditions, comprising:

means for detecting brain waves from a living subject as an electrical brain-wave signal;

means for detecting the amplitude value of the brain-wave signal during each of a plurality of fixed time intervals;

an accumulating storage unit for classifying the detected amplitude values according to magnitude and for accumulating and storing them to prepare a histogram;

a data processor for analyzing the histogram and calculating a standard deviation; and display means for displaying variations in the standard deviation over a time period substantially longer than the time required to obtain one value of the standard deviation, thereby to obtain a display of the trend of said variations.

5. A brain wave analysis apparatus for use in diagnosing living body conditions, comprising:

means for detecting brain waves from a living subject as an electrical brain-wave signal;

means for counting the number of intersections of the brain-wave signal with a zero level within a predetermined period of time; and display means for displaying variations in the count value over a time period substantially longer than said predetermined period of time, thereby to obtain a display of the trend of said variations.

6. A brain wave analysis apparatus according to one of claims 1 to 5 wherein the display means comprises a recorder.

7. A brain wave analysis apparatus according to one of claims 1 to 5, wherein said display means comprises a plurality of memories for storing standard deviations or count values in sequence, and means for periodically reading out all the stored standard deviations or count values from the memories to display them.

8. A brain wave analysis apparatus according to one of claims 1 to 4, wherein the display means comprises an initial value memory for storing the standard deviation at the beginning of a measurement operation, a display for displaying the stored standard deviation, and a display for displaying the latest standard deviation.

9. A brain wave analysis apparatus according to one of claims 1 to 4 including means for displaying the histogram obtained in the accumulating storage unit.

10. A method of diagnosing the condition of a living subject, comprising the steps of detecting brain waves from the living subject in the form of an electrical brain-wave signal;

classifying according to magnitude, accumulating, and storage in a data accumulating storage unit, at least one of the following parameters: (a) the time intervals between adjacent ones of the intersections of the brain-wave signal with a predetermined level, (b) the peak values of the brain-wave signal in the said time intervals, (c) the waveform areas of the brain-wave signal in the said time intervals, and (d) the amplitude value of the brain-wave signal during each of a plurality of constant periods of time, thereby to obtain a histogram;

calculating a standard deviation of the histogram by use of a data processor; and displaying on a real time basis, and over a time substantially longer than the time required to obtain one value of the standard deviation, the variations with time, in said standard deviation, thereby to obtain a display of the trend of said variations.

* * * * *